March 22, [illegible] H. A. JOHNSON, [illegible] Plant Pat. [illegible]

STRAWBERRY PLANT

Filed April 21, 1964

INVENTORS
Harold A. Johnson, Jr.
BY Harold E. Thomas
Townsend and Townsend
attorneys United States Patent Office Plant Pat. 2,612
Patented Mar. 22, 1966

2,612
STRAWBERRY PLANT

Harold A. Johnson, Jr., and Harold E. Thomas, Morgan Hill, Calif., assignors to The Strawberry Institute of California, Morgan Hill, Calif.

Filed Apr. 21, 1964, Ser. No. 361,603
1 Claim. (Cl. Plt.—49)

This invention relates to a new and distinct variety of strawberry plant which is the result of a cross between two Strawberry Institute of California seedling selections numbered C52.3 and F121.7 (both unpatented).

The seedlings resulting from this cross were grown and held in an isolated area in northern California and were there asexually reproduced by means of transplanted runners. Testing of these asexually reproduced plants has been carried out in various parts of California.

Figure 1:
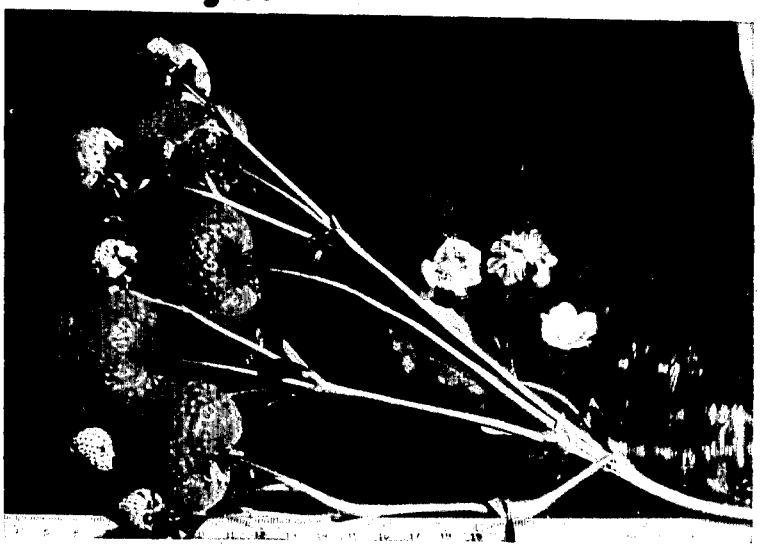
Figure 2:
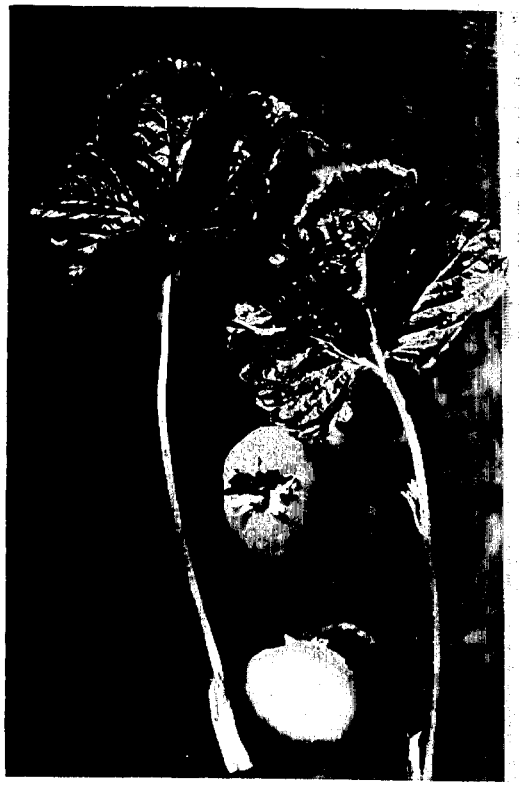

A plant typical of the size, shape and color of the new variety is shown in the accompanying drawing in which:

FIGURE 1 shows (a) typical inflorescence demonstrating the tendency of this variety to ripen all of the berries on a single flower stem at much the same time, and (b) a top view and an under view of a typical blossom; and FIGURE 2 shows (a) two typical leaves, (b) a cross section of the fruit, and (c) a view of a typical ripe berry with the calyx attached.

This new variety of strawberry plant is relatively open crowned and of moderate size and vigor. In this respect it resembles the Goldsmith variety which is described in Plant Patent No. 1,735. This new variety, however, is normally slightly smaller than the Goldsmith variety. Many of the other characteristics of this new variety such as petiole length, leaf size and shape, and serration outline closely resemble those of the Goldsmith variety. The foliage of this new variety and the foliage of the Goldsmith variety are nearly identical in color. Late in the season divergence of color occurs when the Goldsmith variety takes on a darker purplish cast at first and then turns nearly completely purple whereas this new variety remains greener. The leaf surface of this new variety is mildly rugose and is nearly indistinguishable in this characteristic from the Goldsmith variety. Runner production of this new variety in the nursery has normally been good.

The inflorescence of this variety is unique in that frequently there are three secondary peduncles arising from the axial on the primary peduncle instead of two as normally occurs in the Goldsmith variety and other standard varieties. Not all of the plants of this new variety are of this type, but many are, as illustrated in FIGURE 1. This new variety is also distinguished by its tendency to ripen the berries on an inflorescence at nearly the same time with the primaries and secondaries ripening together. This is in contrast to most standard varieties grown in California. The inflorescence is long and holds the fruit beyond or near the edge of the leaf cover. This facilitates picking of the fruit since the berries can be readily found. Primary fruit pedicels often originate at the secondary peduncle axil rather than at the primary axil as occurs in the Goldsmith variety. Some fusing of the secondary and tertiary pedicles occurs along with an occasional fusion of pedicel and secondary peduncle. This has not been observed to occur in the Goldsmith variety. This new variety produces more inflorescences than does the Goldsmith variety, which may be responsible in part for the high yield of berries.

The fruit of this new variety resembles that of the Goldsmith variety but is not consistently as large. It is more distinctly wedge-like in shape and at times may produce a cocks-comb effect at the apex of the wedge. The surface of the fruit is not as smooth as in the Goldsmith variety and irregular folds develop in the surface contour. The fruit during second year of production is much more conic in shape and regular in surface than the first year fruit. The fruit of this new variety does not become as dark when overripe as does the fruit of the Goldsmith variety. The berry has a relatively small core and center cavity. The inside fruit color is very light. The skin firmness is nearly equal to that of the Goldsmith variety throughout most of the year and gives the new variety the ability to stand up well in shipment to distant markets.

The calyx of this new variety tends to be smaller than the calyx of the Goldsmith variety and gives the appearance of being sunken in the flesh of the fruit and receding backward from the depressed area. The calyx is easily removed and often tears away when the fruit is picked. Slight overlap of the sepals may occur but seldom are serrations found in the pointed apex.

Fruit production in this variety is relatively high, comparing favorably with that of the Goldsmith variety. Compared with other everbearing varieties, this new variety is one of the best for yield of spring fruit in that it is one of the earliest of the everbearers with a sizeable crop. Production continues at a high level through the summer and into fall and ceases with the advent of frost. First and second year production patterns are quite similar. Second year fruit is only slightly smaller than first year fruit.

The dessert quality of the fruit of this new variety is considered to be equal to that of the Goldsmith variety. The fruit of this new variety is sweeter than that of the Goldsmith variety.

This new variety is susceptible to mildew, a disease that must be controlled to contain satisfactory growth and production. It is also susceptible to a type of crown degeneration that is occasionally observed in California strawberry fields, the cause of which is unknown. The variety is mildly susceptible to Rhizoctonia root rot and is susceptible to Verticillium wilt. Two-spot mites affect the plant seriously and thrips have been observed to cause flower blasting. In field trials no evidence has accumulated to indicate that susceptibility to virus diseases is a factor in growing this new variety.

For convenience the characteristics of this new variety of strawberry plant as observed in the Monterey Bay area of California are summarized as follows:

*Plant characteristics*

*Foliage.*—The plant is medium to medium-small in size with an open crown and with moderately erect leaves. The longevity and vigor of the plant are rated as medium.

*Root system.*—The root system is of moderate size and vigor.

*Leaves.*—The leaves are of medium size. The central leaflet diameter is usually from five to eight centimeters with the length slightly greater than the width on most leaves. The surface of the leaflets is flat to irregularly wavy and is mildly rugose. The outline of the serrations on the margins of the leaflets is ovate with an acute apex. The color of the upper side of the leaf is Dark Cress Green as shown on Plate XXXI of Ridgway's Color Standards and Nomenclature (1912 edition). The under side of the leaf is Bice Green as shown on Plate XVII of Ridgway. Ageing leaflets may become slightly purplish.

*Petiole.*—The petioles are medium long, usually 13 to 20 centimeters. Bracts may be present on a few petioles.

*Runners.*—Fruiting bed runner production is moderate. Production is variable in the nursery but is normally good. Seasonal variations appear to affect runner formation and occasionally cause low runner development.

*Inflorescence.*—The inflorescences vary in length during the season, becoming progressively longer during the spring and summer and becoming shorter again during the fall. The inflorescences vary in length from 15 to 30 centimeters. There is great variation in length of the main peduncle during the season. Often three secondary peduncles instead of the ordinary two develop from the main peduncle. The primary berry pedicel may origniate from the main axil or from short distance out on one of the secondary peduncles. Fusion of pedicles may be found in this variety wherein the secondary or tertiary pedicles may fuse to secondary or tertiary peduncles, or pedicels may fuse with each other. The inflorescence holds the flower noticeably above the plant at the start of the spring blossoming period but not during the summer or fall period. Hair on the tertiary pedicel 20 millimeters below the flower lays against and is parallel with the pedicel. Pollen production is medium to good during the entire fruiting season.

*Fruit characteristics*

*Size.*—The size of the fruit is medium to medium large with the length of the primaries or well developed secondaries usually from 35 to 40 millimeters and the width usually from 35 to 45 millimeters.

*Shape.*—The fruit is mostly irregularly wedge-shaped but some of the berries are conic. The apex of the wedge at times has a cockscomb outline. The shoulders are rounded out from a sunken calyx during much of the season. The first crop of the two year old plants has a high percentage of conic fruit and less tendency to produce a wedge with cockscomb.

*Surface.*—The surface of the fruit is often furrowed giving the fruit an irregular appearance.

*Color.*—The color of the fruit when ripe is Nopal Red as shown on Plate I of Ridgway. From the surface the color grades to a light pink near the fruit center. The surface is mostly glossy but may lighten in spots during some parts of some crops especially during the peak periods of growth. In general, the fruit does not overdarken when overripe. The color holds well during shipment of the fruit but the fruit is not equal in this characteristic to the Goldsmith variety.

*Core.*—The berry has a relatively small core and center cavity.

*Flesh.*—The berry is firm but juicy and holds its firmness well in shipment but is not equal to the Goldsmith variety in this latter characteristic.

*Seeds.*—The seeds are medium in size and are mostly held even with the fruit surface. They are medium in number. The color of the seeds on the exposed side of the berry is dark reddish while the color of the seeds on the non-exposed side of the berry is Apricot Yellow as shown on Plate IV of Ridgway.

*Calyx.*—The calyx is of medium size varying from 25 to 35 millimeters in diameter. The sepal shape is mainly lanceolate but at times alternates between lanceolate and oblanceolate. At times there is a slight overlap with the smaller sepals overlying the larger sepals. Serrations are rare. The calyx is often, and especially in large fruit, sunk into the flesh in its characteristic manner. At other times it is clasping or held irregularly free of the fruit.

*Flavor.*—The flavor is considered as mild and is subacid and the same generally as Goldsmith, supra. There is no particular aroma to the flesh. The fruit of the new variety is sweeter than Goldsmith, supra.

*Ripening characteristics.*—The primary and the secondary fruit often ripen at the same time as illustrated in FIGURE 1.

The plant above described may vary in slight detail depending upon the climate, the soil and other growth conditions.

We claim:

A new and distinct variety of strawberry plant as herein described and illustrated and characterized particularly by its moderate vigor and medium size, by its medium to medium large fruit varying from conic to wedge in shape, by its ability to produce an early crop when compared to other everbearing varieties, and by its tendency to produce simultaneous ripening of the primary and the secondary fruit on a given inflorescence.

No references cited.

ABRAHAM G. STONE, *Primary Examiner.*